(12) United States Patent
Tuohey et al.

(10) Patent No.: US 11,142,737 B2
(45) Date of Patent: Oct. 12, 2021

(54) CONTINUOUS RECOVERY HARVEST BAG

(75) Inventors: Colin Tuohey, Medway, MA (US); Thomas Erdenberger, Arlington, MA (US); Richard Damren, Marlborough, MA (US); Michael Fisher, Ashland, MA (US); John Swibes, Chesterton, IN (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 31 days.

(21) Appl. No.: 13/402,074

(22) Filed: Feb. 22, 2012

(65) Prior Publication Data

US 2012/0238011 A1 Sep. 20, 2012

Related U.S. Application Data

(63) Continuation of application No. PCT/US2010/046841, filed on Aug. 26, 2010.

(60) Provisional application No. 61/237,286, filed on Aug. 26, 2009, provisional application No. 61/240,323, filed on Sep. 8, 2009.

(51) Int. Cl.
*C12M 1/12* (2006.01)
*C12M 1/00* (2006.01)

(52) U.S. Cl.
CPC ............ *C12M 23/26* (2013.01); *C12M 23/14* (2013.01); *C12M 23/28* (2013.01); *C12M 23/34* (2013.01); *C12M 25/16* (2013.01); *C12M 29/04* (2013.01); *C12M 47/02* (2013.01); *C12M 47/10* (2013.01)

(58) Field of Classification Search
None
See application file for complete search history.

(56) References Cited

U.S. PATENT DOCUMENTS

| | | | | |
|---|---|---|---|---|
| 4,484,936 A | * | 11/1984 | Sakai ................. | B01D 19/0031 210/436 |
| 4,968,624 A | * | 11/1990 | Bacehowski ........ | B65D 77/065 206/484 |
| 4,976,707 A | * | 12/1990 | Bodicky ............. | A61M 5/1483 604/319 |
| 5,057,429 A | * | 10/1991 | Watanabe et al. ......... | 435/297.1 |
| 5,139,946 A | | 8/1992 | Howell et al. | |
| 5,362,642 A | * | 11/1994 | Kern ................... | B67D 7/0288 222/94 |

(Continued)

FOREIGN PATENT DOCUMENTS

| | | | | |
|---|---|---|---|---|
| EP | 725134 | | 7/1996 | |
| FR | 2797887 A1 | * | 3/2001 | ............ C12M 23/14 |

(Continued)

OTHER PUBLICATIONS

Bataille Laurent Guy Francois ."English language translation of FR2797887A1, translated on Aug. 29, 2016".*

(Continued)

*Primary Examiner* — Liban M Hassan
(74) *Attorney, Agent, or Firm* — Grogan, Tuccillo & Vanderleeden, LLP

(57) ABSTRACT

Disclosed herein is a single use continuous recovery, flow-through harvest vessel and corresponding method for harvesting culture medium and simultaneously either leaving the microcarrier beads behind in the vessel or flowing microcarrier beads and medium back into a bioreactor.

12 Claims, 5 Drawing Sheets

(56) References Cited

U.S. PATENT DOCUMENTS

| | | | | |
|---|---|---|---|---|
| 5,749,493 | A * | 5/1998 | Boone | B65D 75/5877 222/105 |
| 5,788,661 | A * | 8/1998 | Japuntich | 604/6.09 |
| 5,792,133 | A * | 8/1998 | Rochat | A61M 1/0001 604/406 |
| 5,858,015 | A * | 1/1999 | Fini | A61J 1/10 128/DIG. 24 |
| 6,099,734 | A * | 8/2000 | Boggs | B01D 63/087 210/263 |
| 6,251,295 | B1 * | 6/2001 | Johnson | A61M 1/3621 210/650 |
| 6,642,019 | B1 * | 11/2003 | Anderson et al. | 435/41 |
| 6,745,902 | B2 * | 6/2004 | Lynn et al. | 210/489 |
| 6,969,367 | B2 * | 11/2005 | Tu | A61M 1/3496 210/321.75 |
| 2003/0036192 | A1 * | 2/2003 | Singh | B01F 11/0017 435/297.2 |
| 2004/0190372 | A1 * | 9/2004 | Goodwin | B01F 13/0818 366/273 |
| 2005/0032205 | A1 * | 2/2005 | Smith | C12M 23/14 435/297.5 |
| 2005/0242114 | A1 * | 11/2005 | Savage | B65D 75/5877 222/92 |
| 2006/0054557 | A1 * | 3/2006 | Hori et al. | 210/645 |
| 2007/0100273 | A1 * | 5/2007 | Kawarabata | A61M 1/3627 604/6.15 |
| 2008/0139865 | A1 | 6/2008 | Galliher et al. | |

FOREIGN PATENT DOCUMENTS

| | | |
|---|---|---|
| WO | 2009115241 | 9/2009 |
| WO | 2009153425 | 12/2009 |

OTHER PUBLICATIONS

International Search Report and Written Opinion, dated Oct. 22, 2010, for PCT/US2010/046841 (the parent case), 9 pages (in English).

Decision on Rejection dated Mar. 12, 2014 on Corresponding Chinese Patent Application No. 201080048344.X.

EP Search Report dated May 3, 2016 from the corresponding EP Application No. 10812625.1.

CN Search Report dated Mar. 23, 2017 from the corresponding CN Application No. 201080048344.X.

* cited by examiner

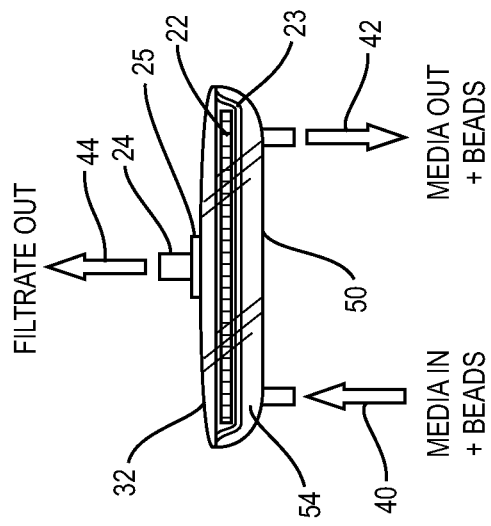
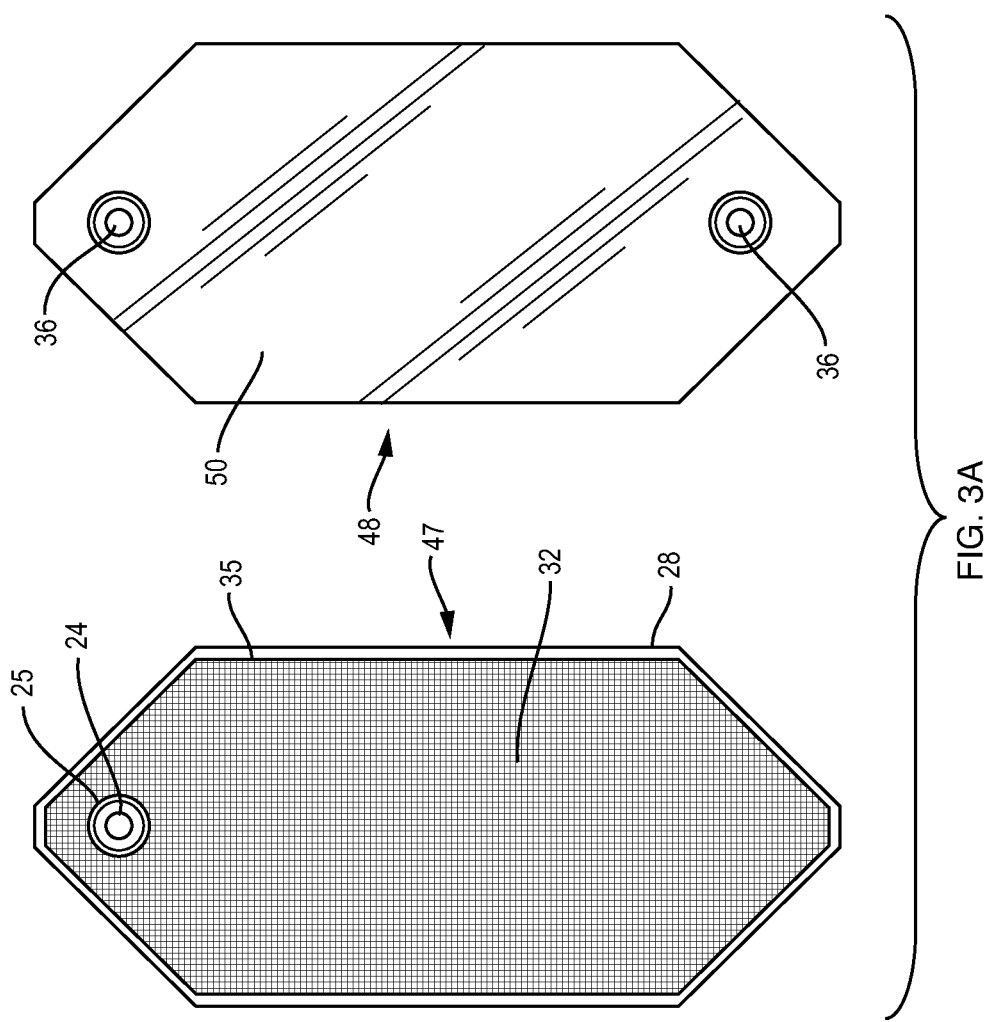
FIG. 3B
FIG. 3A

CONTINUOUS RECOVERY HARVEST BAG

RELATED APPLICATIONS

This application is a continuation of International Application No. PCT/US2010/046841, which designated the United States and was filed on Aug. 26, 2010, published in English, which claims priority to U.S. Provisional Application No. 61/237,286 filed on 26 Aug. 2009 and U.S. Provisional Patent Application No. 61/240,323, filed on Sep. 8, 2009. The entire teachings of the above applications are incorporated herein by reference.

FIELD OF INVENTION

The present disclosure relates to devices and methods for the harvesting of cells grown on microcarriers in, for example, two dimensional disposable bags or three dimensional disposable bench top bioreactor bags, or larger disposable bioreactors.

BACKGROUND

Cell culturing is an essential step in manufacturing biological products such as nucleic acids, viruses for use in vaccines, antibodies, and proteins such as interferons. Anchorage-dependent cells, such as certain animal cells, need to attach to a surface in order to grow and divide.

For large-scale cell culturing, microcarriers provide the large surface area needed for growing anchorage-dependent cells. Van Wezel, in 1967, described the use of microcarriers, small beads or particles about 0.2 mm in diameter, for growing such cells The microcarriers are suspended in a culture medium within a bioreactor bag. Cells (the inoculum) are added to the liquid culture medium in which the microcarriers are suspended. Sometimes gentle agitation is used to help maintain the microcarrier beads in suspension during the cell culturing process.

Non anchorage-dependent cells, termed "suspension cells," do not require a solid support on which to grow, and can grow in a cell suspension.

Continuous or Perfusion Mode: In a continuous or perfusion mode, there is a continuous flow of fresh, nutrient-rich, culture medium through either a microbead suspension with an attached cell population, or through a cell suspension culture. Product is harvested throughout the culture period. Toxic metabolites and sometimes dead cells are removed. In a suspension culture, due to the small size of cells, the process of removing nutrient-depleted medium while retaining cells in a bioreactor presents an ongoing problem. Currently available filtering methods and systems characteristically present several disadvantages, including clogging of the filter and accumulation of dead cells within the bioreactor. These problems affect the amount of product recovered and make it difficult to scale up such perfusion bioreactor systems to an industrial scale.

Batch Mode: In a batch mode, all nutrients are added at the beginning and products are not removed until the end of the batch. Waste products accumulate during the run, and nutrients are used up, making the batch process inefficient for many applications.

Fed-Batch Mode: A fed-batch mode is similar to the batch mode in that products are removed only at the end of the run, but differs in that nutrients are added at multiple intervals during the process.

In each of these modes, the cell population may secrete or shed a product of interest into the culture medium. The product is harvested by removing from the bioreactor bag at least a portion of the culture medium, while leaving behind in the bioreactor bag the cells from the cell suspension or the microcarrier beads with a bound population of cells. As stated above, in the Continuous or Perfusion mode, product is harvested throughout the culture period. In the Batch and Fed-Batch mode, products are removed only at the end of the run In each of these modes of culturing cells, the most conventional way to perform the separation of microcarrier beads or cells from the culture medium during the harvest phase is by letting the beads or cells settle and decanting the fluid, or by externally filtering the mixture. Neither of these methods is efficient and both require a substantial amount of time to accomplish the separation.

An external filter may be used in Normal Flow Filtration (NFF), in which the fluid flow is approximately normal, that is, perpendicular to the filter surface. In addition to the NFF being a relatively slow process, in NFF the particles that do not pass through the filter accumulate and tend to clog the filter.

In Tangential Flow Filtration (TFF) the fluid flow is tangentially along the surface of the filter. In TFF a pressure is applied normal to the filter surface to force a portion of the flowing fluid through the filter to the filtrate side. Rather than clogging the filter, the particles that do not pass through the filter are carried along by the flow. Although such devices do not generally have a clogging problem, the TFF devices require large amounts of area, high flow rates, and high pressures, which may damage cells or the microcarrier beads.

Another method that is not very efficient is related to use of a floating perfusion filter inside of a "rocker" style two dimensional bag. Yet another type of filtration system is a cartridge filter system, which generally includes a corrugated or pleated filter within a cartridge or housing. The cartridge filter also tends to clog readily. None of these currently available systems provide an efficient method for recovering the microcarrier beads.

Thus, there remains an on-going need for an apparatus and method that provide a faster, more efficient means for separating microcarrier beads or cells from the culture medium, and for recovering the microcarrier beads or cells at the time of harvest. The need for such an apparatus and method for use in the continuous or perfusion mode of cell culturing, wherein nutrients are continuously added to the system, and product is harvested throughout the culture period, is particularly well-recognized.

BRIEF SUMMARY OF THE DISCLOSURE

The invention inter alia includes the following, alone or in combination. In one aspect, the present invention relates to our discovery of a harvest and microcarrier recovery bag, and a corresponding method for harvesting culture medium and simultaneously leaving the microcarrier beads behind in the bag, a method that is significantly more efficient than prior art methods. In another embodiment of the invention, media and beads can be flowed out of the harvest and microcarrier recovery bag interior and back into a bioreactor.

The disclosed invention relates to a nonporous vessel capable of holding a fluid, the vessel comprising: an outer wall surface and an inner wall surface, the inner wall surface defining an interior chamber for holding the fluid; a filter having a perimeter, a first surface and a second surface, and fixedly attached around its entire perimeter to a portion of the inner wall surface of the nonporous vessel, thereby forming an integrated interior bag within the nonporous vessel; and a first fitment attached to the outer wall surface of the nonporous vessel at a portion of the outer wall surface that is adjacent to the integrated interior bag, the first fitment forming a first port configured to allow fluid to flow from the interior chamber through the filter into the integrated interior bag, and out of the first port.

In one embodiment the nonporous vessel comprises a flexible material. In another embodiment the nonporous vessel comprises a collapsible bag.

In one embodiment of the invention, the area of the filter is approximately equal to the area of the inner wall surface of the nonporous vessel.

Another embodiment of the invention is a nonporous container having a first interior chamber capable of holding a fluid, the nonporous container comprising: an interior pouch having a second interior chamber and integral with a wall of the nonporous container, the interior pouch comprising a porous surface adjacent to the first interior chamber of the nonporous container and configured such that the first interior chamber and the second interior chamber are in fluid communication with one another; a fitment forming a port on a surface of the nonporous container, the port positioned to allow access to the second interior chamber, such that when the fluid contained in the first interior chamber is allowed to flow out of the port on the surface of the nonporous container, the fluid passes out of the first interior chamber and through the porous surface, forming a filtrate, the filtrate passing through the interior pouch, and out of the port.

The disclosed nonporous vessel may have a tubing attached to the port of a fitment for harvesting the fluid held in the interior chamber of the nonporous vessel.

The present invention has many advantages. There has been an ongoing need to solve problems related to harvesting a culture medium comprising products of interest while leaving microcarrier beads behind in a bioreactor or cell culture bag. One advantage provided by the disclosed invention over the prior art external filter is the minimizing or prevention of clogging of a filter. The external filters are typically used in a "dead end" or batch mode wherein, during harvesting, the microcarrier beads accumulate and eventuially clog the filter. In contrast, the integrated filter of the disclosed harvest and microcarrier recovery bag does not tend to clog readily as does the external filter. The disclosed device can be used in a batch mode or in a continuous or semi-continuous mode, wherein the concentrated microcarrier bead suspension or the cell suspension may be recycled back into the bioreactor.

Another advantage of the disclosed invention is that it is not only faster than settling and decanting the fluid, but also it is a much more effective separation method than decanting. With the decanting method, there is a high likelihood of ineffective separation (i.e. having beads pass into the harvest fluid).

Further, typically with the disclosed device and method, one is able to retrieve more fluid than is possible with decanting. Our previous attempts at using porous tubing assemblies have other limitations such as clogging, and more limited fluid retrieval based on its position in the bag and, when used on a 3-dimensional bag, its occasional entanglement in the impeller.

Further advantage is obtained by integrating the present invention into the bioreactor design or other disposable devices such that both devices are disposable, single use, and sterilized simultaneously, without the risk of contamination via aseptic connections.

BRIEF DESCRIPTION OF THE DRAWINGS

The foregoing and other features and advantages of the invention will be apparent from the following more particular description of illustrative embodiments of the invention, as illustrated in the accompanying drawings. The drawings are not necessarily to scale, emphasis being placed upon illustrating the results of exemplary embodiments of the disclosed apparatus.

FIG. 3A is a top plan view of a top panel 47 of a continuous recovery, flow-through harvest bag. and a bottom plan view of the bottom panel 48 of the bag according to an embodiment of the invention.

FIG. 3B is a cross-sectional view of a continuous recovery, flow-through harvest bag according to an embodiment of the invention.

DETAILED DESCRIPTION

Figure 1:
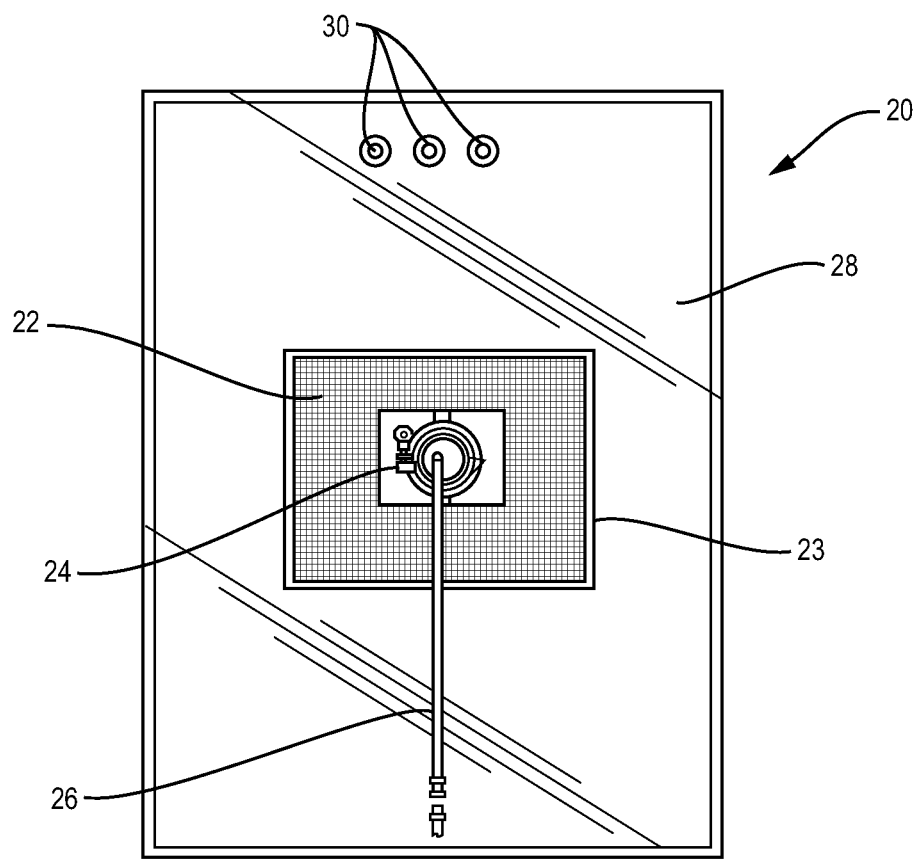
FIG. 1 is a schematic drawing of a top plan view of a section of a harvest and microcarrier recovery vessel in the form of a two dimensional, collapsible bag having a rectangular shaped filter and screen that are partially visible through the transparent bag according to an embodiment of the invention.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

In contrast to prior art methods for separating microcarrier beads from a culture medium, the inventors of the present subject matter have now discovered a continuous recovery harvest vessel or bag and corresponding method for harvesting culture medium and simultaneously leaving the microcarrier beads behind in the harvest and microcarrier recovery bag, or in the bioreactor, or in both the harvest and microcarrier recovery bag, and the bioreactor, a method that is significantly more efficient than prior art methods.

The invention relates to a vessel, which can be a collapsible bag that performs a specific function for a filtration application. The bag can be of any size. In one embodiment the collapsible bag is chosen from a two dimensional disposable bag, a three dimensional disposable bench top bioreactors bag, and a disposable bioreactor. In another embodiment of the invention, the bag is a single use, flexible, nonporous bag suitable for culturing cells on microcarrier beads.

The disclosed continuous recovery harvest vessel can be a disposable or single use. The terms "continuous recovery harvest vessel," "harvest and microcarrier recovery bag," "nonporous vessel," and "nonporous bag" are used synonymously herein.

In another embodiment of the invention, the bag is a flexible, nonporous bag suitable for harvesting the medium of a cell culture.

In yet another embodiment of the invention depicted in FIGS. 3A, 3B, 4, and 5, the nonporous bag is a continuous recovery, flow-through harvest bag that could be used, for example, with a continuous or perfusion mode culture of cells in a bioreactor. In one embodiment, of the flow-through harvest bag, media and microcarrier beads can be flowed from a bioreactor into a port in the bottom panel of the flow-through bag and out of another port in the bottom panel of the bag and back into the bioreactor.

In one embodiment the nonporous bag comprises a flexible polyethylene material or film, and may have fitments attached to it. The term "fitment" as used herein refers to a separate object that is welded, e.g., heat welded to the nonporous bag film in order to attach it. As such, a fitment often comprises a polymeric material which can be the same or similar to the polymeric material comprising the wall of the nonporous bag. A fitment is often a more dense material than the wall of the nonporous bag, and may be added to the bag to enable a functionality. A non-limiting example of a fitment is one that forms a port. In one embodiment of the invention, a port as described below is added to the wall of the nonporous bag in order to withdraw cell culture medium or other fluid from the interior of the nonporous bag.

The disclosed nonporous bag may have a tubing attached to the port of the fitment for harvesting the fluid held in the interior chamber of the nonporous bag.

The nonporous bag may have a plurality of fitments configured with ports and tubing used to flow culture medium containing microcarrier beads or a cell suspension in a continuous fashion through the apparatus such that a continuous filtration occurs as the culture medium flows from the interior chamber through the integrated interior bag, through the filter, and out of the port.

In various embodiments of the invention the nonporous bag is a two dimensional disposable bag comprising a top panel and a bottom panel, or a three dimensional disposable bench top bioreactor bag, or a disposable bioreactor bag for use with a support structure. The nonporous bag can be any size, for example, 10 liters, 100 liters, 200 liters, 500 liters, or 5000 liters.

In one embodiment of the invention the nonporous bag comprises a nonporous polymeric material including at least one interior wall portion to which a sheet of porous polymeric material is directly attached around the entire outer perimeter of the filter by welding, for example, heat welding. The attached filter is positioned completely inside the nonporous bag and forms an integrated, interior bag within the nonporous bag. One side of the filter is exposed to the bulk fluid that is contained in the nonporous bag. A pocket is formed on the other side of the filter between the filter and the interior wall portion of the nonporous bag.

FIG. 1 is a schematic drawing of a top plan view of a section of a two dimensional harvest and microcarrier recovery bag 20 according to an embodiment of the invention. A rectangular, microporous filter, referred to herein as a "filter" 23 is attached to the inner wall surface of the transparent, nonporous bag 20. The edge of filter 23 and a screen 22 are visible through the transparent top panel 28 of nonporous bag 20. A tubing 26 is attached to the harvest port of a fitment 24. Additional ports 30 may be used for filling the nonporous bag, sparging, or probes for sensors, for example.

Figure 2A:
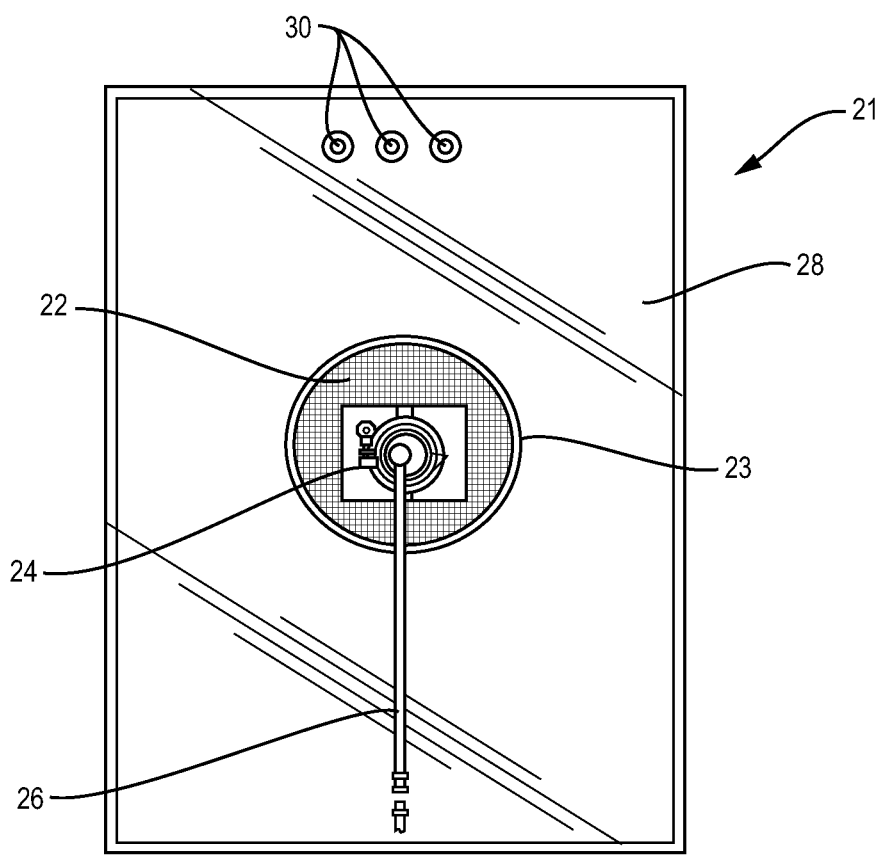
FIG. 2A is a schematic drawing of a top plan view of a section of a two dimensional harvest and microcarrier recovery bag having a circular shaped filter and screen that are partially visible through the transparent bag according to an embodiment of the invention.

FIG. 2A depicts a top plan view of another embodiment of a harvest and microcarrier recovery bag 21. The only difference between the nonporous bag shown in FIG. 1 and in FIG. 2A is that the filter in the nonporous bag 21 shown in FIG. 2A is circular or oval-shaped.

Figure 2B:
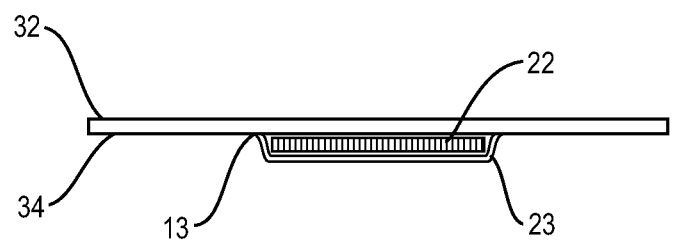
FIG. 2B is a cutaway view of a portion of the top panel of a harvest and microcarrier recovery bag showing a screen sandwiched between the filter and the interior wall of the bag according to an embodiment of the invention.

FIG. 2B is a cutaway view of a portion of the top panel 28 of the disclosed single use harvest and microcarrier recovery bag 21 showing bag exterior wall surface 32, the bag interior wall surface 34, the filter 23 that is seam-welded at 13 to the interior wall surface 34 around the entire perimeter of the filter 23, and the free-floating screen 22 sandwiched between the filter 23 and the interior wall surface 34 of the bag 21 according to an embodiment of the invention.

The screen 22 and the filter 23 may each comprise any suitable material, for example, an integrated polyethylene of a suitable porosity. The screen 22 may be free-floating and placed between the filter 23 and the interior wall surface 34 of the bag 21, and the filter 23 seam-welded around its perimeter to the interior wall surface 34 of the bag 21, thereby forming a sandwich inside the bag 21. FIG. 2B shows that the seam welded at 13 around the perimeter of the filter 23 forms, within the nonporous bag 21, an integrated interior bag having a porous wall, the porous wall facing the interior chamber of the nonporous bag 21.

FIG. 3A provides both a top plan view 47 of the top panel 32 of a continuous recovery, flow-through harvest bag 28, and a bottom plan view 48 of the bottom panel 50 of the bag 28 according to an embodiment of the invention. A harvest port 24 is formed at a fitment 25 in the exterior top panel 32 of bag 28. A screen (22 in FIG. 3B) is free-floating between filter 23 and the inner wall surface of top panel 32. A screen-filter-bag sandwich 35 is formed in the top panel of the bag 28. The bag 28 is a continuous recovery, flow-through harvest bag 28 that could be used, for example, with a continuous or perfusion mode culture of cells in a bioreactor (not shown). In the embodiment shown in FIGS. 3A and 3B, the area of the filter is approximately equal to the entire area of the inner wall surface of the top wall panel of the two dimensional disposable bag.

In one embodiment of the flow-through harvest bag 28, media and microcarrier beads can be flowed from a bioreactor into one of ports 36 in the bottom panel 50 of the flow-through bag 28. See, for example, FIG. 3B, which is a cross-sectional view of a continuous recovery, flow-through harvest bag 28 according to an embodiment of the invention. In FIG. 3B the bag interior 54 is bounded on one side by the bottom panel 50. Arrow 40 indicates the direction of flow of media and microbeads (or cells) through a port and into the bag interior 54. Arrow 42 shows the direction of flow of media and beads out of the bag interior 54 through another port, and back into a bioreactor (not shown). Arrow 44 shows the direction of flow of media out of the bag, leaving the beads behind in the bag.

The cross-sectional view in FIG. 3B shows the free-floating screen 22 sandwiched between the filter 23 and the top panel 32 of the bag 28. The filter 23 is shown welded at its periphery to the top panel 32 of bag 28, thereby forming an integral filter bag with the top panel 32 of the bag 28. The screen 22 simply serves to hold the filter 23 away from the top panel 32. In both FIG. 3A and FIG. 3B, a fitment 25 and harvest port 24 are shown in the top panel 32. In FIG. 3A, one of the ports 36 can be used to flow media and beads from the bioreactor into the bag 28, and one of the ports 36 can be used to flow media and beads back out of bag 28 and into the bioreactor.

Figure 4:
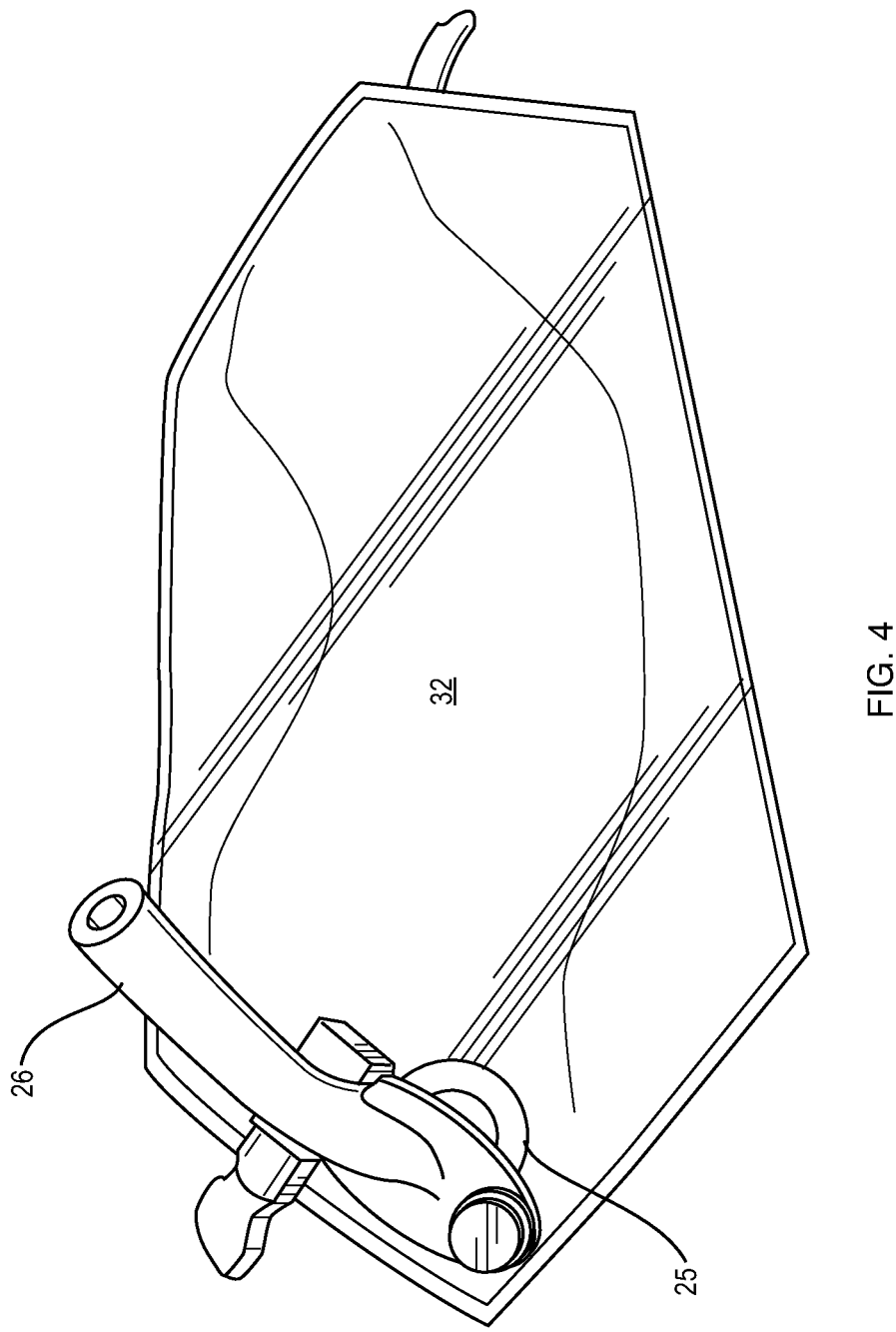
FIG. 4 depicts a perspective view of the top of a continuous recovery, flow-through harvest bag according to an embodiment of the invention.

FIG. 4 is a perspective view of the top of a two-dimensional, continuous recovery, flow-through harvest bag according to an embodiment of the invention. The top panel 32 has a fitment 25 for a harvest port and tubing 26 attached to the harvest port.

Figure 5:
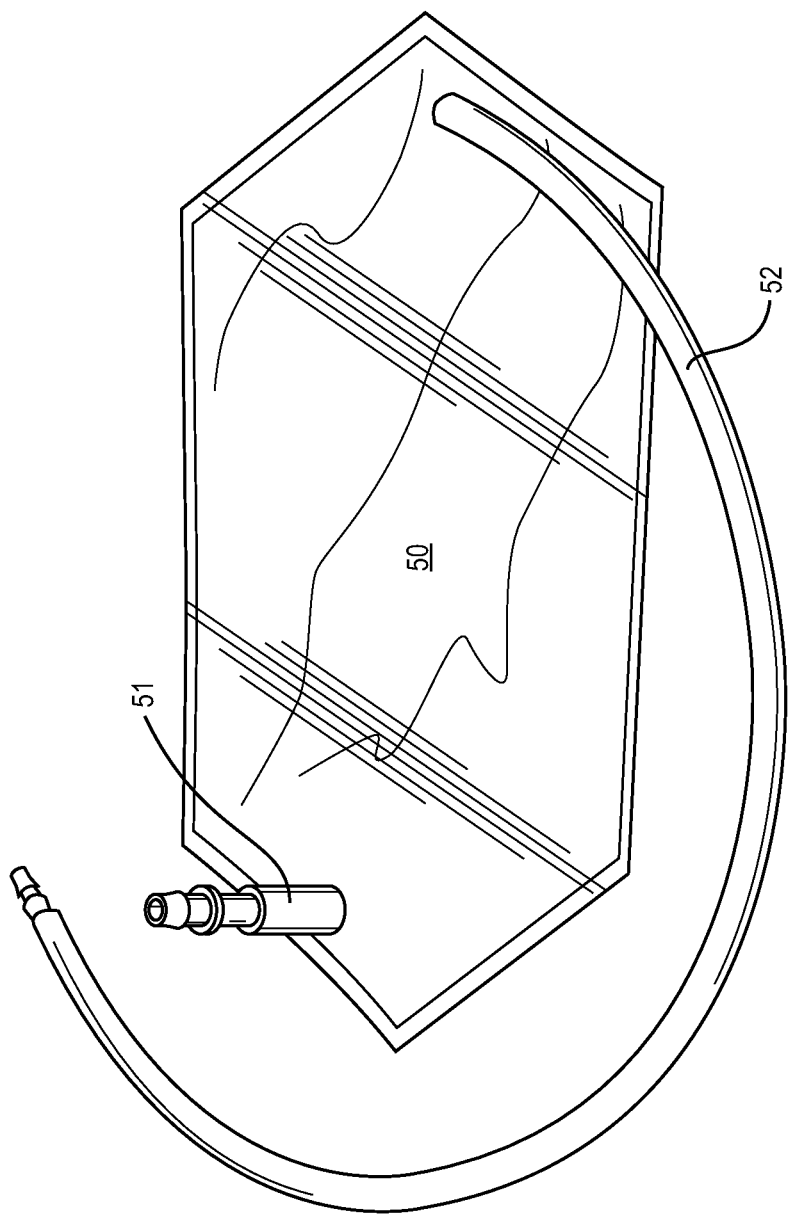
FIG. 5 is a perspective view of the bottom of a continuous recovery, flow-through harvest bag according to an embodiment of the invention.

FIG. 5 is a perspective view of the bottom panel 50 of the continuous recovery, flow-through harvest bag shown in FIG. 4. Fitment 51 can be for attaching a delivery tube for flowing media and beads from a bioreactor into the bag. Tubing 52 can be for flowing media and beads out of the bag and back into the bioreactor operating in a continuous, perfusion mode.

The fitment comprising the harvest port 24 with tubing 26 attached is connected to the wall portion of the nonporous bag 28 such that when fluid such as the culture medium is drawn out of the interior portion of the nonporous bag 28 through the tubing 26, the bulk fluid in the nonporous bag 28 must first pass through the integrated, interior bag within the nonporous bag 28, and through the filter or filter 23 before exiting the nonporous bag 28 through port 24 and entering the tubing 26. The filter 23 is fully integrated with the nonporous bag 28, and allows the fluid to pass through while retaining in the nonporous bag 28, via mechanical sieving, all particles, such as microcarrier beads, above a certain particle size.

The area of the filter 23 may be any size, for example it may be approximately equal to the area of the inner wall surface of the bag 28.

In another embodiment of the invention the area of the filter 23 is equal to from about 2 percent to about 95 percent of the area of the inner wall surface of the nonporous bag 28. In yet another embodiment of the invention the area of the filter is equal to from about 25 percent to about 50 percent of the area of the inner wall surface of the nonporous bag 28.

In a preferred embodiment of the invention the nonporous bag 28 includes a free-floating screen 22 positioned between the filter 23 and the inner wall surface of the bag 28. In one embodiment the screen 22 has an average pore size that is greater than the average pore size of the filter 23. The average pore size of the filter can be, for example, from about 0.2 micrometers to about 200 micrometers.

The screen 22 helps to hold the filter 23 away from the inner wall surface of the bag. The screen 22 is visible through the transparent top surface of the bag 28.

FIG. 2A depicts another embodiment of the nonporous bag 28 wherein the filter 23 is circular in shape.

The filter 23 of the disclosed nonporous bag may comprise an integrated polyethylene filter or high density polyethylene (HDPE). Other non-limiting examples of polymers that may be available in a porous form and that may be suitable material from which the filter 23 may be formed include, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, and copolymers thereof, or physical blends thereof.

Another non-limiting example of a porous material that would be suitable for use in a filter according to an embodiment of the invention is a porous matrix prepared from collagen and chondroitin sulfate with some cross-linking with glutaraldehyde. Yet another example is a a high-molecular-weight polymer of polylactide or polylactic acid (PLA).

In one embodiment of the invention the filter 23 may be an integrated polyethylene filter. The pore size can depend on the choice of microcarrier bead size or other particles that are targeted to remain behind in the nonporous bag as the fluid is drawn out through the filter. A typical pore size may be, for example, from about 0.2 micrometers to about 200 micrometers.

Nonlimiting examples of applications for which the disclosed single use harvest and microcarrier recovery bag may be used include separation of microcarrier beads from the cell culture medium, harvest separation of cells from the cell culture medium, or perfusion culture.

EXEMPLIFICATION

To prepare a single use harvest and microcarrier recovery bag, we heat welded a microporous polymeric sheet around its entire perimeter to a portion of the inside of the wall of a flexible, nonporous bag, thereby forming an integrated, interior bag comprising one wall which comprises a portion of the flexible, nonporous bag, and a second wall which comprises the microporous polymeric sheet. The porous wall of the interior bag is in contact with the interior of the flexible, nonporous bag. The nonporous wall of the interior bag comprises the portion of the nonporous flexible bag to which it is attached around its entire perimeter. The nonporous bag we used was a polyethylene bag.

We added fitments, including a fitment forming a harvest port, to the outside of the nonporous bag. We did not weld any fitments directly to the filter. The fitment was also formed from polyethylene, but of a higher density than that of the nonporous bag. The fitment can be any of a variety of sizes and shapes depending on various factors. The prototypes we constructed utilized a one-half inch (0.5 inch) hose barb or a 3 inch sanitary fitting as the fitment.

When in use for a separation of microcarrier beads from a culture medium, the porous wall of the integrated, interior bag within the nonporous bag acts as a filter to separate microcarrier beads from the rest of the solution in the bag. Fluid can be pumped out of the interior chamber of the nonporous bag, through the integrated, interior bag, through the microfilter 23, and out the harvest port 24 into the harvest tubing 26, leaving the microbeads behind in the interior chamber.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawing), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. An apparatus, comprising:
a nonporous vessel capable of holding a fluid, the nonporous vessel comprising:
a planar top wall panel and a planar bottom wall panel joined directly to the top wall panel about an entire periphery of the top wall panel, the top wall panel and the bottom wall panel lying in registration with one another and forming a two-dimensional structure when in a non-expanded state, the top wall panel and the bottom wall panel being formed from a non-rigid flexible material, the top panel and the bottom panel defining an entire outer wall surface and an inner wall surface of the nonporous vessel, the inner wall surface defining an interior chamber for holding a fluid;
a filter having a perimeter, a first surface and a second surface, and fixedly attached around its entire perimeter to the top wall panel the nonporous vessel, thereby forming an integrated interior culture medium bag within the nonporous vessel;
a screen positioned within the integrated interior culture medium bag and free-floating between a portion of the filter not fixedly attached to the portion of the inner wall surface of the nonporous vessel and a portion of the inner wall surface of the nonporous vessel adjacent to and not fixedly attached to the filter, the screen having an average pore size that is greater than the average pore size of the filter;
a first fitment attached to the outer wall surface of the nonporous vessel at a portion of the outer wall surface that is adjacent to the integrated interior culture medium bag, the first fitment forming a first port allowing for fluid to flow out of the nonporous vessel through the first port after flowing through the filter and into the integrated interior culture medium bag; and
a second fitment attached to the outer wall surface of the nonporous vessel at a portion of the outer wall surface that is not adjacent to the integrated interior culture medium bag, the second fitment forming a second port allowing for fluid to flow into the nonporous vessel and into the interior chamber;
a third fitment attached to the outer wall surface of the nonporous vessel at a portion of the outer wall surface that is not adjacent to the integrated interior culture medium bag, the third fitment forming a third port allowing for fluid to flow out of the nonporous vessel after flowing out of through the interior chamber;
a plurality of additional ports in the outer wall surface of the nonporous vessel for at least one of filling the nonporous vessel, sparging and/or probes for sensors, the plurality of additional ports being in addition to the first port, the second port and the third port;
wherein the nonporous vessel is configured for connection to a bioreactor through the second fitment and the third fitment to allow continuous fluid circulation and recycling of the fluid between the bioreactor and the interior chamber, wherein the nonporous vessel is configured to separate particles from a culture medium flowing through the nonporous vessel;
wherein the portion of the outer wall surface to which the third fitment is attached is the same portion of the outer wall surface to which the second fitment is attached;
wherein the second fitment and the third fitment are located at opposite ends of the portion of the outer wall surface to which the second fitment and third fitment are attached so as to facilitate filtration of the fluid;
wherein the first fitment and the second fitment are configured such that fluid flow into the nonporous vessel through the second fitment is parallel to and in the same direction as the fluid flow out of the nonporous vessel through the first fitment; and
wherein the third fitment is configured such that fluid flow out of the nonporous vessel through the third fitment is parallel to and in the opposite direction as the fluid flow through the first fitment and the second fitment; and
wherein the first fitment, the second fitment and the third fitment are oriented perpendicularly to a planar surface defined by the top wall panel and the bottom wall panel, respectively, of the non-porous vessel, so as to direct a flow of fluid therethrough in a direction that is perpendicular to the planar surface defined by the top wall panel and the bottom wall panel, respectively.

2. The apparatus of claim 1, wherein the first fitment, the second fitment and the third fitment are each attached to one of the top wall panel and the bottom wall panel.

3. The apparatus of claim 1, wherein the non-porous vessel is a collapsible bag.

4. The apparatus of claim 1, wherein an area of the filter is approximately equal to an entire area of the inner wall surface of at least one of the top wall panel and the bottom wall panel of the nonporous vessel.

5. The apparatus of claim 1, wherein an area of the filter is equal to from about 2 percent to about 95 percent of an entire area of the inner wall surface of at least one of the top wall panel and the bottom wall panel of the nonporous vessel.

6. The apparatus of claim 5, wherein the area of the filter is equal to from about 25 percent to about 50 percent of an area of the inner wall surface of the nonporous vessel.

7. The apparatus of claim 1, wherein the filter is an integrated polyethylene filter.

8. The apparatus of claim 1, wherein the average pore size of the filter is from about 0.2 micrometers to about 200 micrometers.

9. The apparatus of claim 1, comprising a tubing for harvesting the fluid held in the interior chamber of the nonporous vessel, the tubing attached to the first fitment of the first port.

10. The apparatus of claim 1, wherein an area of the filter is approximately equal to an entire area of the inner wall surface of the top wall panel.

11. An apparatus, comprising:
a nonporous collapsible bag container having a planar top panel and a planar bottom panel joined directly to the top panel about a periphery of the top panel, the top panel and the bottom panel lying in registration with one another and forming a two-dimensional structure when in a non-expanded state, the top panel and the bottom panel being formed from a non-rigid flexible material, and a first interior surface defining a first interior chamber capable of holding a fluid, the nonporous collapsible bag container comprising:

a porous surface perimetrically attached to the first interior surface of the nonporous collapsible bag container;

an interior pouch having a second interior chamber and integral with a wall of the nonporous collapsible bag container, the interior pouch defined between a portion of the porous surface not attached to the first interior surface of the nonporous collapsible bag container and the first interior surface of the nonporous collapsible bag container adjacent to and not attached to the porous surface and configured such that the first interior chamber and the second interior chamber are in culture medium fluid communication with one another through said porous surface;

a screen positioned within the second interior chamber and free-floating between a portion of the porous surface not attached to the first interior surface of the nonporous collapsible bag and a portion of the interior surface of the nonporous collapsible bag adjacent to and not attached to the porous surface, the screen having an average pore size that is greater than the average pore size of the porous surface;

a fitment forming a harvest port in the top panel, the harvest port positioned to allow access to the second interior chamber, such that when the fluid contained in the first interior chamber is allowed to flow out of the harvest port on the surface of the nonporous collapsible bag container, the fluid passes out of the first interior chamber and through the porous surface and forms a filtrate that passes-through the interior pouch and out of the harvest port in the top panel; and a second port and a third port formed in the bottom panel of the nonporous collapsible bag container, each of said second and third ports positioned to allow access to the first interior chamber and located at opposing ends of the bottom panel of the nonporous collapsible bag container, the second port allowing fluid flow into the first interior chamber and the third port allowing fluid flow out of the first interior chamber;

a plurality of additional ports in an outer wall surface of the nonporous collapsible bag for at least one of filling the nonporous collapsible bag, sparging and/or probes for sensors, the plurality of additional ports being in addition to the harvest port, the second port and the third port;

wherein the non-porous container is configured for connection to a bioreactor through the second port and third port to allow fluid flow to continuously circulate and recycle between the bioreactor and the first interior chamber so as to provide filtration of the fluid, wherein the nonporous collapsible bag is configured to separate particles from a culture medium flowing through the nonporous collapsible bag;

wherein the second port and the third port are configured so as to direct a flow of fluid into and out of the nonporous collapsible bag container in a direction that is perpendicular to a planar surface defined by the bottom panel; and wherein the top panel and the bottom panel are transparent.

12. A nonporous vessel capable of holding a fluid, the nonporous vessel comprising:

a planar top panel and a planar bottom panel joined to the top panel about an entire periphery of the top panel, the top panel and the bottom panel lying in registration with one another and forming a two-dimensional structure when in a non-expanded state, the top panel and the bottom panel defining an outer wall surface and an inner wall surface of the nonporous vessel, the inner wall surface defining an interior chamber for holding a fluid;

a filter having a perimeter, a first surface and a second surface, and fixedly attached around its entire perimeter to the top panel, thereby forming an integrated interior culture medium bag within the nonporous vessel, the filter having an area of about 25 percent to about 50 percent of an area of the inner wall surface of the nonporous vessel and an average pore size of about 0.2 micrometers to about 200 micrometers;

a screen positioned within the integrated interior culture medium bag and free-floating between a portion of the filter not fixedly attached to the portion of the inner wall surface of the nonporous vessel and a portion of the inner wall surface of the nonporous vessel adjacent to and not fixedly attached to the filter, the screen having an average pore size that is greater than the average pore size of the porous surface;

a first fitment attached to the outer wall surface of the nonporous vessel at a portion of the outer wall surface that is adjacent to the integrated interior culture medium bag, the first fitment forming a first port configured to allow fluid to flow from the interior chamber through the filter into the integrated interior culture medium bag, and out of the first port;

a second fitment attached to the outer wall surface of the nonporous vessel at a portion of the outer wall surface that is not adjacent to the integrated interior culture medium bag, the second fitment forming a second port configured to allow fluid to flow into the interior chamber; and a third fitment attached to the outer wall surface of the nonporous vessel at a portion of the outer wall that is not adjacent to the integrated interior culture medium bag, the third fitment forming a third port configured to allow fluid to flow out of the interior chamber;

a plurality of additional ports in the outer wall surface of the nonporous vessel for at least one of filling the nonporous vessel, sparging and/or probes for sensors, the plurality of additional ports being in addition to the first port, the second port and the third port;

wherein the portion of the outer wall surface to which the third fitment is attached is the same portion of the outer wall surface to which the second fitment is attached; and wherein the second fitment and the third fitment are located at opposite ends of the portion of the outer wall surface to which the second fitment and third fitment are attached so as to facilitate filtration of the fluid within the vessel;

wherein the top panel and the bottom panel are each formed from a flexible material;

wherein the second fitment and the third fitment are oriented so as to direct a flow of fluid into and out of the nonporous vessel in a direction that is perpendicular to a planar surface defined by the bottom panel and/or the filter, wherein the nonporous vessel is configured to separate particles from a culture medium flowing through the nonporous vessel;

wherein the first fitment, the second fitment and the third fitment are each attached to one of the top panel and the bottom panel; and wherein the filter is operative to retain particles disposed in the fluid via mechanical sieving;

wherein the top panel and the bottom panel are transparent.

\* \* \* \* \*